(12) United States Patent
Jaroszeski et al.

(10) Patent No.: US 6,221,665 B1
(45) Date of Patent: Apr. 24, 2001

(54) ELECTROFUSION CHAMBER

(75) Inventors: Mark J. Jaroszeski; Richard A. Gilbert; Richard Heller, all of Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/328,833

(22) Filed: Jun. 8, 1999

Related U.S. Application Data

(60) Provisional application No. 60/088,758, filed on Jun. 10, 1998.

(51) Int. Cl.⁷ .................................................. C12N 15/87
(52) U.S. Cl. ........................................ 435/450; 435/285.2
(58) Field of Search .................................... 435/449, 450, 435/453, 454, 285.1, 285.2

(56) References Cited

FOREIGN PATENT DOCUMENTS

3505147 A1  10/1986  (DE) .

OTHER PUBLICATIONS

Jaroszeski et al (Biophysical Journal, vol. 67, Oct. 1994, 1574–1581).

Jaroszeski, M.J., Gilbert, R.A., and Heller, R. (1994). *Analytical Biochemistry* 216:271–275.

Detection and Quantitation of Cell–Cell Electrofusion Products by Flow Cytometry; Mark J. Jaroszeski, Richard Gilbert, Richard Heller, Jul. 14, 1993, pp. 271–275.

Mechanically Facilitated Cell–Cell Electronfusion, Mark J. Jaroszeski, Richard Gilbert, Paul G. Fallon, Richard Heller, Biophysical Journal, vol. 67, Oct. 1994, pp. 1574–1581.

*Primary Examiner*—James Ketter
(74) *Attorney, Agent, or Firm*—Kohn & Associates

(57) ABSTRACT

A new and useful apparatus for producing cell electrofusion is provided. The apparatus comprises:

a. a chamber with a substrate disposed therein, b. means for directing the cells to be fused toward one side of the substrate in so that the cells in the fluid medium are retained against the one side of the substrate with a significant portion of the cells in cell-to-cell contact with each other along said one side of the substrate, and c. a device for inducing fusion of the portion of the cells in cell-to-cell contact with each other along the predetermined portion of the one side of the substrate.

20 Claims, 2 Drawing Sheets

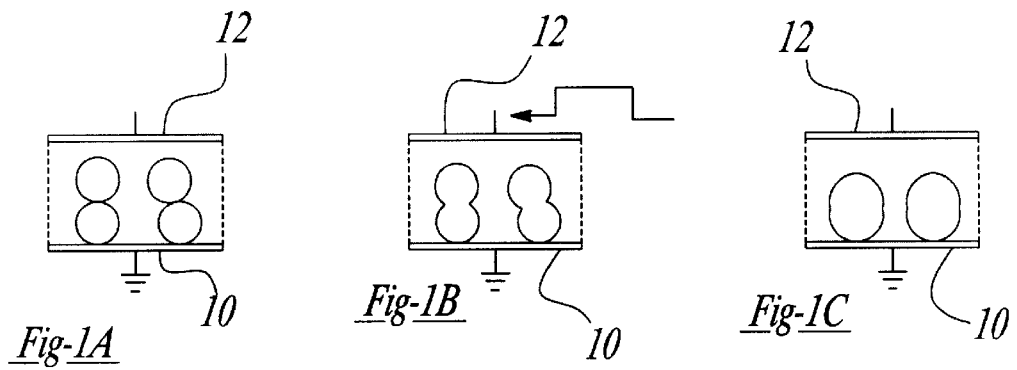
*Fig-1A*  *Fig-1B*  *Fig-1C*
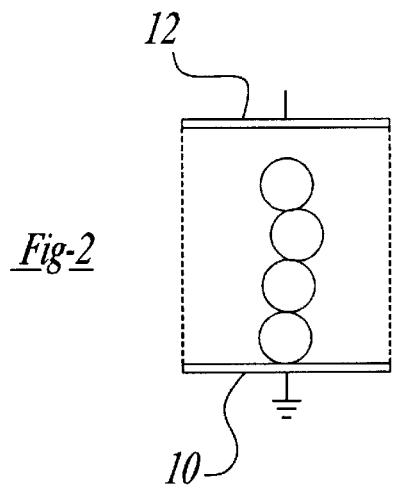
*Fig-2*
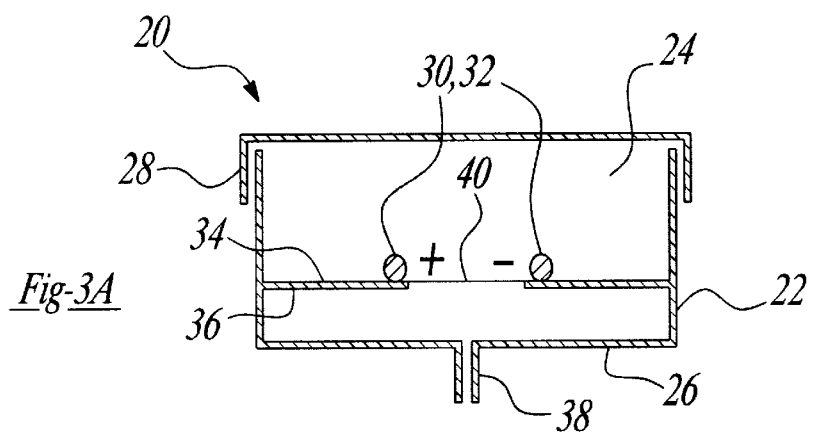
*Fig-3A*
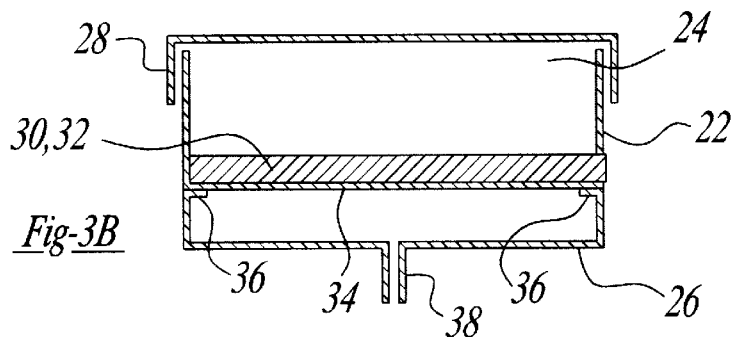
*Fig-3B*

ELECTROFUSION CHAMBER

This application claims the benefit of U.S. Provisional Application No. 60/088,758, filed Jun. 10, 1998.

TECHNICAL FIELD

The present invention relates to an electrofusion chamber, and particularly to a disposable electrofusion chamber which is used to provide a simple, inexpensive and efficient way of performing electrofusion.

BACKGROUND

Electrofusion is the common name for procedures that induce fusion of living cells using electricity. Cell-cell electrofusion (CCE) is the generic term used to describe electrofusion of living cells. CCE can refer to fusion of one cell type to a different cell type, or it can refer to fusing cells of the same type. In this application, reference to fusion of cells is intended to encompass both fusion of different cell types and also fusion of the same cell types. Moreover, it is intended to encompass the fusion of two or more cells to each other.

CCE processes generally involve three principal steps. First, fusion partners (i.e., two or more cells to be fused to each other) must be forced into contact with each other between two electrodes or some other means of inducing electrofusion. The cells must be in an electrically conductive medium. Second, one or more electrical pulses are applied to the cells that are in contact between the electrodes. Electrical pulses induce fusion and are administered by creating and maintaining a potential (voltage) difference across the electrodes. CCE is usually achieved using direct current (DC) pulses. The third and final CCE step occurs naturally; fused cells anneal into one cell due to their normal fluidity. CCE processes do not normally yield 100% fusion. Typically, a fraction of the contacted cells are induced to fuse while the remaining fraction does not fuse. Also, many of the extensively used methods involve steps which have a high rate of cell killing.

Most existing commercial CCE devices and applications known to the applicants use a process called dielectrophoresis to cause cell-cell contact. Dielectrophoresis is the application of alternating current (AC) to cause fusion partners to line up in chains between the electrodes. Thus, cell-cell contact is achieved at the points where adjacent cells in a chain are touching. Dielectrophoresis is incorporated into the first step of the three-step fusion process described above. After chains have formed, one or more DC pulses are delivered to induce fusion and the cells are allowed to anneal.

Jaroszeski et al., (Biophysical Journal, Vol. 67, Oct. 1994, 1574–1581) discloses apparatus and methods developed to enable mechanically facilitated cell-cell electrofusion to be performed. The apparatus and methods mechanically place cells in contact before fusion. A novel fusion chamber is disclosed composed of two functionally identical electrodes that are housed in a multi-layer structure. The layers function as a support for the electrodes. They also allow adjustment of the distance between opposing electrode faces. The electrodes were constructed to allow cells to be deposited, by vacuum, onto each face. The electrode faces were positioned at a predetermined distance from each other to mechanically force cell-cell contact between the deposited cells. Fusion was induced by delivering direct current pulses to the juxtaposed cells.

Jaroszeski et al. (Analytical Biochemistry, 216, 271–275 (1994)) discloses a cytometric method for detecting and quantitating hybrid cells that resulted from cell-cell electrofusion. Cells from two different lines and two vital fluorescent dyes were used in conjunction with a flow cytometer to demonstrate the method.

The German Patent Publication DE 3505147 A1 to Strellrecht et al. discloses an electrofusion process wherein cells are fixed on a first and second carrier. The two carriers are arranged so that the cells that are fixed to the respective carriers are opposite relative to each other. The cells are moved toward each other forming pairs of cells, one from each carrier. The pairs are each fused.

It would be advantageous to provide more efficient and effective means for inducing cell-to-cell contact and fusion than that described above. The present invention provides improved means for inducing such cell-cell contact and uses electric pulses applied from a different direction relative to deposited cells than prior art.

SUMMARY OF THE PRESENT INVENTION

The present invention provides a new and useful electrofusion device which is designed to be a convenient, inexpensive, and easy-to-use device that can be used to force cell-cell contact and to induce fusion of at least a portion of the cells in cell-to-cell contact. This device can be produced as a single and/or multiple use device, it is easily sterilized, it can be made as a disposable device, and does not require the use of AC.

Fusion without AC has significant benefits. For example, an electrofusion device that requires only a DC generator represents a lower initial equipment investment than is generally required for dielectrophoresis equipment. Moreover, the high cost of generators that produce AC and DC may discourage some researchers from using electrofusion. The present invention solves that problem by requiring only DC voltage, thereby enabling performance of electrofusion without the AC generator costs associated with conventional dielectrophoresis devices.

Additionally, the device of the present invention is flexible, in the sense that it can be operated from the DC power supply of various electric cell manipulator devices. For example, many laboratories use a physical phenomenon that is related to fusion in order to manipulate cells. This phenomenon is called electroporation. Specifically, it is common for researchers to perform both electrofusion and electroporation. However, electric pulse generators for electroporation produce DC pulses only. Thus, an inexpensive electrofusion chamber that does not require AC makes electrofusion possible for facilities that already have DC pulse generators.

The fact that in both of the foregoing examples the need for AC is eliminated also has biological relevance. Specifically, other devices known to applicants utilize a phenomenon called dielectrophoresis induced by AC of relatively long duration (e.g. seconds and/or minutes) to achieve cell-cell contact. Elimination of long duration AC is biologically advantageous because it can directly cause cellular damage. Also, heat generated during dielectrophoresis can be damaging to the cells.

According to the present invention, an apparatus for producing electrofusion of two types of cells comprises:
  a. chamber with a substrate that is used as a surface for achieving cell-cell contact,
  b. a mechanism for directing cells to be fused contained in a fluid medium toward one side of the substrate in such a manner that a substantial amount of cells are drawn to and retained against the one side of the substrate with a portion of the cells in cell-to-cell contact with each other along the one side of the substrate, and c. a device for inducing fusion of a portion of the cells in cell-to-cell contact with each other over the predetermined portion of the one side of the substrate.

The device for inducing fusion preferably comprises a DC voltage, which is preferably disposed to apply an electric field to the substrate in an orientation which is parallel to the one side of the substrate. The DC voltage source is preferably applied to a pair of electrodes spaced apart along a predetermined portion of the side of the substrate, to apply DC voltage to the cells in cell-to-cell contact between the pair of electrodes.

The means for drawing the cells toward one side of the substrate can be achieved in two preferable ways that both achieve the same result. The first employs a porous substrate and a vacuum source. The vacuum source is configured to apply a level of vacuum to the fluid medium that is sufficient to draw a significant portion of the fluid medium through the substrate while retaining the cells on one side of the substrate in cell-to-cell contact. The vacuum source is configured to induce this migration of the cells and also to retain enough medium mixed with the cells to preserve the viability of the cells to be fused. The second configuration employs a charged substrate with a selected polarity that will attract cells of opposite polarity to one side of the substrate.

The chamber is preferably designed so that it can be operated from the DC power source of a conventional dielectrophoresis device having both an AC current source and a DC voltage source. The device can also be operated from a DC power source of the type typically associated with an electroporation device, or from various other types of DC power sources found in other facilities.

These and other features of the present invention will become further apparent from the following detailed description and the accompanying drawings.

BRIEF DESCRIPTION OF DRAWINGS

FIGS. 1a–1c schematically elaborate certain underlying principles of electrofusion;

FIG. 2 schematically illustrates principles of a machine for performing dielectrophoresis;

FIGS. 3A and 3B are schematic cross-sectional views of a device for performing electrofusion according to the principles of the present invention at 90 degrees to each other;

DETAILED DESCRIPTION

Figure 4:
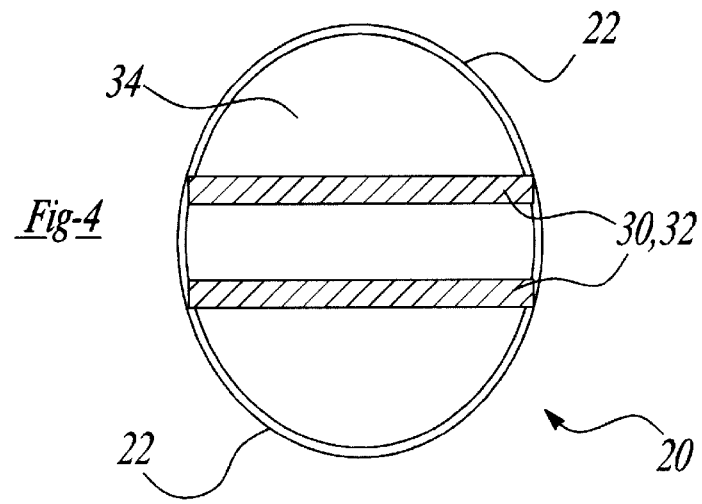
FIG. 4 is a schematic top view of the device of FIG. 3, taken from the direction 4—4.

As described above, electrofusion is the common name for procedures that induce fusion of living cells using electricity. Cell-cell electrofusion (CCE) is the generic term used to describe electrofusion of living cells. CCE can refer to fusion of one cell type to a different cell type, or it can refer to fusing cells of the same type. In this application, reference to fusion of two types of cells is intended to encompass both fusion of different cell types and also fusion of the same cell types. Moreover, while the description below relates to fusion of two cells, it is contemplated that the principles of this invention can be used to fuse two or more cells.

Generally, electrofusion is performed by applying one or more direct current pulses to closely juxtaposed cells. Unipolar and bipolar pulses have been used. Pulses may be administered as a train of identical or different pulses. The currently accepted scientific explanation of CCE is based on the principle of dielectric breakdown. When a biological cell is subjected to electric fields, a transmembrane potential is induced. This induced potential is superposed on the naturally occurring transmembrane potential maintained by the cell. The natural potential is commonly called the resting potential. In physical terms, these potentials are ions that accumulate on either side of the membrane. Ions of one polarity are on one side, and ions of the opposite polarity are on the other side. If the potential across the membrane is high enough then the membrane will dielectrically break down as a result of the force of attraction between the separated ions of opposite polarity. This type of breakdown results in temporary structural defects in the lipid bilayer structure and depolarization of the membrane. The defects have been described as pores and pore-like structures because it has been observed that molecules that do not normally enter to cytosolic compartment can gain access to the cell interior after cells have been electrically treated. The structural defects are temporary as normal membrane fluidity enables cells to reseal membrane defects to regain an intact membrane. The fusion of two or more cells is facilitated by maintaining close cell-to-cell contact when cells are electrically treated so that membrane defects that occur in both cells in the area of contact will enable both cell membranes to reseal as one.

CCE processes generally involve three principal steps. Referring to FIG. 1a, fusion partners (i.e., two types of cells to be fused to each other) must be forced into contact with each other between two electrodes 10, 12. The cells must be in an electrically conductive medium. Second, one or more electrical pulses are applied to the cells that are in contact between the electrodes (see FIG. 1b). Electrical pulses induce fusion and are administered by creating and maintaining a potential (voltage) difference across the electrodes. CCE is usually achieved using direct current (DC) pulses. The third and final CCE step occurs naturally; fused cells anneal into one cell due to their normal fluidity (see FIG. 1c). CCE processes do not normally yield 100% fusion. Typically, a fraction of the contacted cells are induced to fuse while the remaining fraction does not fuse.

As illustrated in FIG. 2, with a typical dielectrophoresis machine, application of alternating current (AC) is used to cause fusion partners to line up in chains between the electrodes 10, 12. Thus, cell-cell contact is achieved at the points where adjacent cells in a chain are touching. After chains have formed, one or more DC pulses are delivered to induce fusion and the cells are allowed to anneal.

FIGS. 3A, 3B, 4 and 5 show different views of a chamber 20 for performing electrofusion according to the principles of the present invention. The chamber 20 includes a molded chamber body 22 and a cap 28. The container 22 is cylindrical with an open top 24 and a bottom 26 and serves as a housing for the internal components. The cap 28 covers the top of the body 22 to complete the chamber 20. The internal components of the chamber 20 include two electrodes 30, 32, a porous substrate 34, a substrate support 36, is and a port 38 for connection to a vacuum source.

Cell-cell electrofusion is conducted in the chamber 20 by first placing a suspension of cells between the two electrodes 30, 32. Then, vacuum is applied. The vacuum is sufficient to draw liquid from the suspension toward one side 40 of the substrate 34 and through the pores of the substrate, but not so complete as to evacuate all of the liquid medium, so that the cells in the suspension remain substantially viable. This draws deposits and maintains layers of cells on the one side 40 of the substrate. This will result in cells in contact with each other in the space between the two electrodes 30, 32. After deposition, one or more DC pulses are administered to the electrodes 30, 32 to induce fusion of cells that are in cell-to-cell contact between the electrodes. The electric field produced by the DC pulses will be substantially parallel to the substrate 34.

Figure 5:
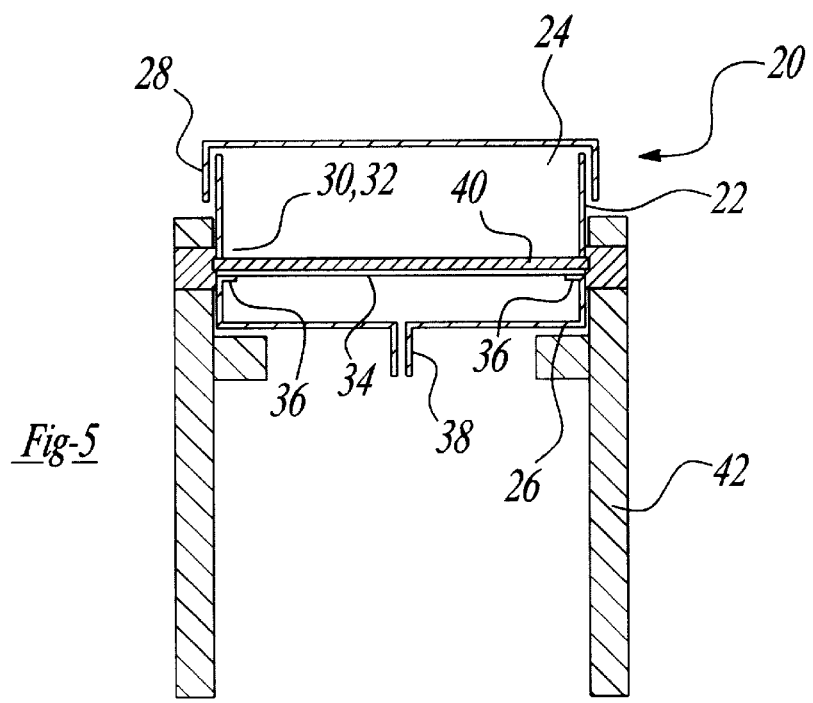
FIG. 5 is a schematic cross-sectional view of a chamber according to the present invention supported on a reusable stand, and further illustrates how electrical connections are made.

An additional feature of the invention is a reusable stand 42 that is designed to hold the chamber during use. The stand is depicted in FIG. 5. The stand is a means of holding the small chambers in a manner that allows easy access to the vacuum port and also a simple means of connecting an electrical generator to the chamber. A stand that fulfills these criteria also reduces the complexity and cost of the disposable chambers. This is because pulse generator connections and a means of holding the small chamber need not be built into the disposable chamber.

The chamber described above is a very flexible and functional design that can be applied to many different situations. For example, as illustrated in FIGS. 3, 4 and 5, the container 22 is cylindrical, the porous substrate 34 is circular, and the electrodes 30, 32 extend across a portion of the container. However, it is contemplated that the container could have other geometric forms (e.g. it could be rectangular in cross section) and the substrate could have a configuration to match the configuration of the container. Moreover, 1. the physical size of the chamber can be adjusted to accommodate fusion of small numbers of cells or large number of cells;
2. the pore size and number of pores per unit area in the substrate can be adjusted, depending on the cell type under investigation;
3. electrode size and spacing can be adjusted to accommodate various electrofusion parameters. For example, a chamber can be designed with an electrode gap that is wide enough for only two mammalian cells to fit between them (approximately 20 micrometers). Performing fusion in this manner would greatly increase the yield of fusion products that consist of two cells.

An example of the way an electrofusion chamber can be built and operated to perform electrofusion is described below:

1. Mold, extrude, or machine the body of the chamber out of a nonelectrically conductive material such as plastic and which, when required, can be sterilized utilizing methods known in the art.
2. Provide a porous surface for deposition of cells. A mesh, porous membrane, or other porous material can be utilized. The applicants have utilized polycarbonate track etch membranes (Poretics Inc.).
3. Provide two or more electrodes for delivering electric pulses to the cells that are deposited on the porous surface. These can be of any shape or size. The inventors suggest parallel stainless steel electrodes that can be of circular or rectangular cross-sectional areas. These electrodes should be placed on the porous surface prior to cell deposition, placed immediately adjacent to the cells after deposition, embedded in the porous surface, and/or embedded in the substrate support.
4. Provide a vacuum source generated from a standard vacuum pump, suction bulb, or syringe. A means for attaching the vacuum source to the port for vacuum connection should also be provided. (No special characteristics of the vacuum pump.) Alternatively, pressure can be applied to the side of the chamber that contains the cells in order to cause or force migration of the cells toward one side of the membranes.
5. Provide a means for connecting a DC pulse generator to the electrodes.
6. Provide a DC generator that is capable of delivering current to the electrodes. Commercially available electroporation and electrofusion generators that deliver DC pulses can be used; however, use is not limited to these generators.

One way of operating the device is as follows:

1. Prepare a suspension of living biological cells containing one or more different types of cells that the user desires to fuse.
2. Remove cap from device and transfer a desired quantity of cells into the fusion chamber.
3. Apply vacuum to draw the cells into contact with each other on the porous membrane. The inventors have found that vacuums in the range of 25 to 150 mmHg are useful; however, other degrees of vacuum can be used.
4. Apply DC electricity to induce fusion between the juxtaposed cells. The exact electrical parameters for inducing fusion are dependent on the type(s) of cells that the user wishes to fuse. Some parameters that have been shown to work are: 1–10 rectangular pulses with pulse durations ranging from microseconds to milliseconds. The magnitude of the field generated in these cases ranges from hundreds of volts per centimeter to thousands of volts per centimeter.
5. After pulse delivery, fused cells are washed out of the chamber using a carrier solution such as, but not limited to, physiologic saline.

The prototype constructed and used as described above was used to fuse rat N1-S1 hepatocellular carcinoma cells (American Type Culture Collection, CRL-1604). Prior to introducing the cells into the chamber, one-half of the cells were stained with 5-chloromethylfluorescein (CMFDA, Molecular Probes, Eugene, Oreg.) which is a green fluorescing compound. The remaining half of the cells were stained with 5-(and 6)-((( 4-chloromethyl)benzoyl)amino) tetramthylrhodamine (CMTMR, Molecular Probes) which is a red fluorescing compound. Equal parts of the green and red fluorescing cells were mixed together and then introduced into the fusion chamber. Fusion products were identified using flow cytometry as those hybrids that exhibited both red and green fluorescence (Jaroszeski, M. J., Gilbert, R. A., and Heller, R. (1994) Detection and quantitation of cell-cell electrofusion products by flow cytometry *Analytical Biochemistry* 216: 271–275). A table of resulting data is given below.

| Electrical Treatment | Mean Percent Dual Fluorescing Hybrids | Standard Deviation |
| --- | --- | --- |
| No Pulses | 2.08 | 0.314 |
| 8 DC Pulses, 100 µs each, 1500 V/cm field strength | 5.62 | 3.44 |
| 8 DC Pulses, 100 µs each, 2000 V/cm field strength | 7.85 | 2.82 |
| 8 DC Pulses, 100 µs each, 3000 V/cm field strength | 9.08 | 6.64 |
| 4 DC Pulses, 100 µs each, | 8.6 | 0.82 |

-continued

| Electrical Treatment | Mean Percent Dual Fluorescing Hybrids | Standard Deviation |
|---|---|---|
| 2000 V/cm field strength 4 DC Pulses, 100 µs each, 3000 V/cm field strength | 5.52 | 3.21 |

Figure 6:
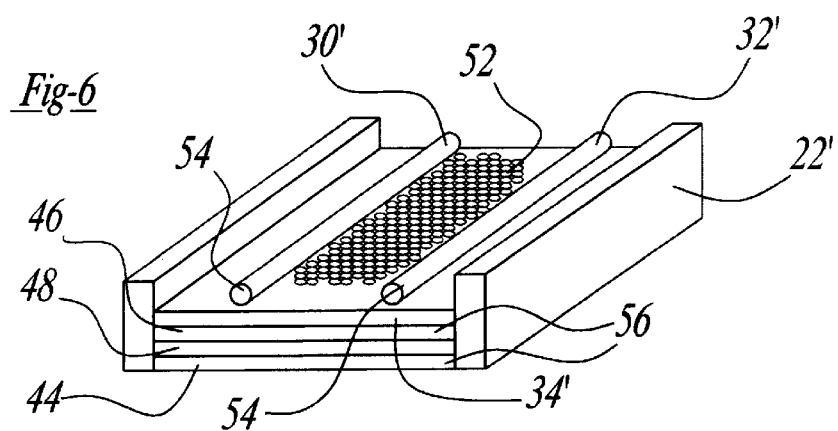
FIG. 6 is a schematic perspective view of a further embodiment of a chamber made in accordance with the present invention.

The above description applies to using an electrofusion chamber that employs a porous substrate and a vacuum source to cause cells to migrate to one side of a substrate to achieve cell-to-cell contact. As previously mentioned, a charged substrate 34' can be used to achieve migration and subsequent cell-to-cell contact, as shown in FIG. 6 (like primed numbers are used to show like members between the different embodiments shown). Most biological cells have a surface charge (negative). Providing a substrate 26' with a surface charge of opposite polarity (positive) causes migration from a fluid medium to the surface of the substrate 36'. A surface charge can be imparted on a substrate by means of an electrical and/or mechanical circuit. Surface charges are also a natural occurrence or imparted as part of a manufacturing process. The use and function of a fusion chamber that employs a charged substrate is similar to the description above except that no vacuum is applied.

Referring specifically to FIG. 6, the substrate 34' is comprised of conductive plates 44, 46 separated by a dielectric 48. Above the uppermost conductive plate 46 is a plate of non-conductive material 34' that serves as the substrate. The cells 52 are deposited in contact with each other between the two electrodes 30', 32', the electrodes delivering fusogenic pulses. A DC pulse generator 54 is operatively connected to the electrodes 30', 32' while means for providing a voltage 56 is operatively connected to the conductive plates 44, 46. Thusly, this embodiment of the invention provides a charged substrate as a surface for achieving cell-to-cell contact.

Moreover, modifications to the electrofusion chamber described above can be made without departing from the concept of the present invention. For example, while vacuum and charged substrates are described for drawing cells to the one side of the substrate, it is contemplated that other devices (e.g. devices using magnetic bead separation principles) could be used to draw the medium containing the cells toward the one side of the substrate and hold the cells in cell-to-cell contact against the one side of the substrate while a fusogenic DC potential is applied to those cells. In addition, rather than drawing the cell containing medium to the substrate, all containing medium can be pressurized to force it against the substrate. Moreover, other types of means for inducing fusion of cells on the one side of the substrate are contemplated. For example, a magnetically induced electric field could be used to induce fusion. Further, chemical means (e.g. using polyethylene glycol) could also be used to induce fusion. It should be noted that the electrodes do not serve a purpose for PEG induced fusion. Other surface active agents that disrupt cell membranes which can be used to induce fusion.

Based on the above, the present invention is distinguishable from the prior art. Based on the prior art, cells are deposited on two porous surfaces (as set forth in the patents cited in the background art section above), the surfaces are moved together, and an electric field (DC pulses) is applied in the direction that is perpendicular to the plane of the substrates used for deposition. According to the present invention, cells are deposited onto one substrate surface and pulses are applied in a direction that is parallel to the surface of the substrate. This provides a simpler design to practice the process in that it is easier to use the present invention. It is also much simpler to make, as the prior art requires a very precise movement mechanism and measurement of gap between two surfaces with cells on them. The present invention includes no moving parts and no dimensions that are critical down to the micron level as required by the prior art.

Further, points of fusion in the present invention take advantage of the areas of cell-to-cell contact of adjacent cells in the same plane as the substrate. The prior art requires multiple layers of cells sandwiched between two substrates. Finally, the present invention can be made with much less cost due to lack of moving parts and critical dimensions compared to the prior art assemblies. The present invention can be made disposable whereas the prior art would be far too costly to be disposable. This is critical in practicing the invention in an environment that requires sterility which is best facilitated by a single use disposable device.

Accordingly, there has been described above an electrofusion chamber which is believed to be simple and efficient, and which, according to the preferred embodiment, does not require an AC generator. However, it is believed possible to utilize an AC generator to achieve cell-to-cell fusion, using the chamber and other principles of the present invention, if the AC generator is utilized for very short time periods (e.g. less than seconds), so as not to cause the biological problems described above. With the foregoing disclosure in mind, it is believed other forms of electrofusion chambers embodying the principles of the present invention will become apparent to those in the art.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of effecting cell-cell fusion comprising the steps of (a) providing a chamber with a substrate and a fluid medium containing cells, (b) migrating at least some of the cells toward one side of the substrate, and (c) fusing a portion of the migrated cells in cell-to-cell contact in proximity to the one side of the substrate.

2. A method as defined in claim 1, wherein the step of migrating the cells comprises charging a selected polarity to the one side of the substrate and attracting cells having an opposite polarity toward the one side of the substrate.

3. A method as defined in claim 2, wherein said step of providing a charge of selected polarity to the one side of the substrate comprises providing a positive charge to the one side of the substrate.

4. A method as defined in claim 1, wherein the substrate is porous, and wherein the step of migrating the cells comprises creating a pressure gradient between the one side of the substrate and at least a portion of the cells in the vicinity of the one side of said substrate, the one side of said substrate being at a lower pressure than the portion of the cells in the vicinity of the one side of the substrate, so that the cells migrate toward the one side of the substrate.

5. A method as defined in claim 1, wherein the substrate is porous, and wherein the step of migrating the cells further comprises applying a vacuum to a selected part of the porous substrate; producing a low pressure region in the vicinity of the selected part of the substrate, and causing cells to migrate toward the low pressure region in the vicinity of the selected part of the substrate.

6. A method as defined in claim 1, wherein said fusing step further comprises the step of applying an electromagnetic field across a predetermined portion of the one side of the substrate, the electromagnetic field being configured to induce fusion of a portion of the cells in cell-cell contact within said electromagnetic field.

7. A method as defined in claim 1, wherein said fusing step is further defined as applying a fusogenic chemical to the substrate.

8. Apparatus for producing cell fusion, comprising:
   (a) a chamber having a substrate,
   (b) a fluid medium for containing cells to be fused which are disposed in said chamber,
   (c) means for inducing migration of cells in said chamber toward one side of said substrate, and
   (d) means for inducing fusion of at least a portion of the cells which have migrated toward said one side of said substrate.

9. Apparatus as defined in claim 8, wherein said means for inducing migration of cells comprises means for producing a charge of a selected polarity on said one side of said substrate to cause cells of opposite polarity to migrate toward said one side of said substrate.

10. Apparatus as defined in claim 9, wherein said means for producing a charge on said one side of said substrate comprises a charging device.

11. Apparatus as defined in claim 10, wherein said charging device comprises a charging circuit, and said substrate is formed of conductive material and is incorporated into said charging circuit.

12. Apparatus as defined in claim 10, wherein said charging device includes at least one element which produces an electromagnetic field located proximate to said substrate such that said one side of said substrate is disposed within said electromagnetic field, thereby to induce said charge of selected polarity on said one side of said substrate.

13. Apparatus as defined in claim 8, wherein said means for inducing migration of cells comprises a substrate formed of a material which has a natural charge and/or acquires and retains an electrostatic charge of a selected polarity during its production, said selected polarity being of opposite polarity to the polarity of cells in the chamber, thereby to induce migration of such cells of opposite polarity toward said substrate.

14. Apparatus as defined in claim 8, wherein said means for inducing migration of cells comprises charging means on the opposite side of said substrate, said substrate and said charging circuit being configured for charging of selected polarity to be applied to one side of said substrate, thereby to induce migration of cells of opposite polarity toward said one side of said substrate.

15. Apparatus as defined in claim 9, wherein said selected polarity is a positive polarity.

16. Apparatus as defined in claim 9, wherein said substrate comprises a plate formed of substantially non-conductive material, and said charging circuit comprises a pair of conductive plates with a dieletric material there between.

17. Apparatus as defined in claim 16, wherein said selected polarity is a positive polarity.

18. Apparatus as defined in claim 8, wherein said substrate is formed of a porous material, and said means for inducing migration of cells toward said one side of said substrate comprises means for applying a vacuum to a selected part of the porous substrate for producing a low pressure region in the vicinity of the selected part of the substrate, and causing cells to migrate toward the low pressure region of the vicinity of the selected part of the substrate.

19. Apparatus as defined in claim 8, wherein said means for inducing cell-to-cell fusion comprises means for applying an electromagnetic field across a predetermined portion of the one side of the substrate, said electromagnetic field being configured to induce fusion of a portion of the cells in cell-cell contact within said electromagnetic field.

20. Apparatus as defined in claim 8 wherein said means for inducing cell-to-cell fusion includes fusogenic chemicals.

* * * * *